US012630843B2

(12) United States Patent
Martín Molina et al.

(10) Patent No.: US 12,630,843 B2
(45) Date of Patent: May 19, 2026

(54) POLYNUCLEOTIDE FOR PHYSIOLOGICAL EXPRESSION IN T-CELLS

(71) Applicant: FUNDACIÓN PÚBLICA ANDALUZA PROGRESO Y SALUD, Seville (ES)

(72) Inventors: Francisco Martín Molina, Seville (ES); María Tristán Manzano, Seville (ES); Noelia Maldonado Pérez, Seville (ES); Pedro Justicia Lirio, Seville (ES)

(73) Assignee: FUNDACIÓN PÚBLICA ANDALUZA PROGRESO Y SALUD, Seville (ES)

( * ) Notice: Subject to any disclaimer, the term of this patent is extended or adjusted under 35 U.S.C. 154(b) by 558 days.

(21) Appl. No.: 18/246,173

(22) PCT Filed: Sep. 21, 2021

(86) PCT No.: PCT/ES2021/070684
§ 371 (c)(1),
(2) Date: Mar. 21, 2023

(87) PCT Pub. No.: WO2022/058640
PCT Pub. Date: Mar. 24, 2022

(65) Prior Publication Data
US 2024/0043868 A1 Feb. 8, 2024

(30) Foreign Application Priority Data

Sep. 21, 2020 (ES) ................................ ES202030954
Sep. 21, 2020 (ES) ................................ ES202030955

(51) Int. Cl.
| | |
|---|---|
| *C12N 15/86* | (2006.01) |
| *A61K 40/11* | (2025.01) |
| *A61K 40/31* | (2025.01) |
| *A61K 40/42* | (2025.01) |
| *C07K 14/725* | (2006.01) |
| *C07K 16/28* | (2006.01) |
| *C12N 5/0783* | (2010.01) |

(52) U.S. Cl.
CPC .............. *C12N 15/86* (2013.01); *A61K 40/11* (2025.01); *A61K 40/31* (2025.01); *A61K 40/4211* (2025.01); *C07K 14/7051* (2013.01); *C07K 16/2803* (2013.01); *C12N 5/0636* (2013.01); *C07K 2319/03* (2013.01); *C12N 2510/00* (2013.01); *C12N 2740/16043* (2013.01); *C12N 2830/008* (2013.01); *C12N 2830/15* (2013.01)

(58) Field of Classification Search
None
See application file for complete search history.

(56) References Cited

U.S. PATENT DOCUMENTS 4,683,195 A 7/1987 Mullis et al.

FOREIGN PATENT DOCUMENTS

| | | |
|---|---|---|
| CN | 108018312 A | 5/2018 |
| CN | 110055281 A | 7/2019 |
| WO | 2018213332 A1 | 11/2018 |
| WO | 2020099572 A1 | 5/2020 |

OTHER PUBLICATIONS

Roberts et al (Mammalian Synthetic Promoters, Methods in Molecular Biology 1651:93-112, 2017).*
Eyquem et al., "Targeting a CAR to the TRAC locus with CRISPR/Cas9 enhances tumour rejection," Nature 543:113-117, Mar. 2017. (19 pages).
Tristan-Manzano et al., "Externally-Controlled Systems for Immunotherapy: From Bench to Bedside," Frontiers in Immunology 11(2044):1-17, Sep. 2020. (17 pages).

* cited by examiner

*Primary Examiner* — Brad Duffy
(74) *Attorney, Agent, or Firm* — Seed Intellectual Property Law Group LLP

(57) ABSTRACT

The invention relates to an improved system for generating immunotherapeutic T-cells comprising a chimeric antigen receptor (CAR).

10 Claims, 4 Drawing Sheets

Specification includes a Sequence Listing.

A)

B)

C)

POLYNUCLEOTIDE FOR PHYSIOLOGICAL EXPRESSION IN T-CELLS

REFERENCE TO AN ELECTRONIC SEQUENCE LISTING

The contents of the electronic sequence listing (370084_403USPC_SeqListing_Revised.txt; Size: 6,088 bytes; and Date of Creation: Oct. 10, 2023) is herein incorporated by reference in its entirety.

FIELD OF THE INVENTION

The present invention relates to a new technology for generating immunotherapeutic T-cells. In particular, the invention provides an improved system for generating immunotherapeutic T-cells comprising a chimeric antigen receptor (CAR).

BACKGROUND OF THE INVENTION

Adoptive immunotherapy, which involves the transfer of autologous antigen-specific T-cells generated ex vivo, is a promising strategy for treating viral infections and cancer. The T-cells used for adoptive immunotherapy can be generated by means of the expansion of antigen-specific T-cells or the redirection of T-cells by means of genetic engineering. The transfer of viral antigen-specific T-cells is a well-established method which is used for the treatment of transplant-associated viral infections and virus-related rare malignant neoplasms. Similarly, the isolation and transfer of tumor-specific T-cells have proven successful in the treatment of melanoma.

New specificities have been successfully generated in T-cells by means of transgenic T-cell receptor or chimeric antigen receptor (CAR) gene transfer. CARs are synthetic receptors consisting of a targeting moiety associated with one or more signaling domains in a single fusion molecule. Generally, the binding moiety of a CAR consists of an antigen-binding domain of a single-chain antibody (scFv), comprising lumen 25 and variable fragments of a monoclonal antibody attached together by a flexible linker. Binding moieties based on receptor or ligand domains have also been used successfully. The signaling domains for first-generation CARs are derived from the cytoplasmic region of Fc or CD3zeta receptor gamma chains. First-generation CARs have been proven to successfully redirect T-cell cytotoxicity, however, they failed to provide a prolonged expansion and 30 anti-tumor activity in vivo. The signaling domains of co-stimulatory molecules including CD28, OX-40 (CD134), and 4-1BB (CD137) were added alone (second generation) or in combination (third generation) to improve the survival and increase the proliferation of CAR2-modified T-cells. CARs have allowed T-cells to be successfully redirected against antigens expressed on the surface of tumor cells of different neoplasms, including lymphomas and solid tumors. CD19 has been presented as an attractive immunotherapy target because most B-cell acute lymphoblastic leukemia (B-ALL) 5 uniformly expresses CD19, whereas the expression is absent in non-hematopoietic cells, as well as in myeloid cells, red blood cells, T-cells, and bone marrow stem cells. Clinical trials targeting CD19 in malignant B-cell tumors are in progress with encouraging anti-tumor responses. Most of them involve the infusion of T-cells genetically modified to express a chimeric antigen receptor (CAR) with specificity derived from the scFv region of a CD19 FMC63-specific mouse monoclonal antibody. However, there is still a need to improve the CAR construct such that it exhibits improved compatibility with T-cell proliferation in order to allow cells expressing such CARs to reach a significant level of clinical advantage. In this sense and despite the obvious benefit for patients treated with CAR-T, current technologies which use 15 strong promoters to express CAR have a negative side. Serious side effects, including the death of patients, mainly due to a cytokine release syndrome (SRC) associated with CAR-T cell hyper-activity in the first few days following infusion, have been reported. Furthermore, a significant percentage of initially responsive patients relapsed as a result of a reduced longevity (and efficacy) of the administered CAR-T cells. Eyquem, Mansilla-Soto et. al. 20 have already proven that TCR type expression improves the anti-leukemia activity of CAR-T cells by using genome edition systems to express transgenes through the promoter of the TRAC locus. However, genome edition strategies use highly sophisticated technologies that are hard to implement in clinical practice.

Therefore, it is necessary to develop polynucleotides which imitate the expression pattern of TCR in a very precise manner, which result in a 3- to 4-fold reduction of the expression of the transgene 8-24 h following T-cell activation, and which recover their expression again after 48-72 h.

3

Figure 1A:
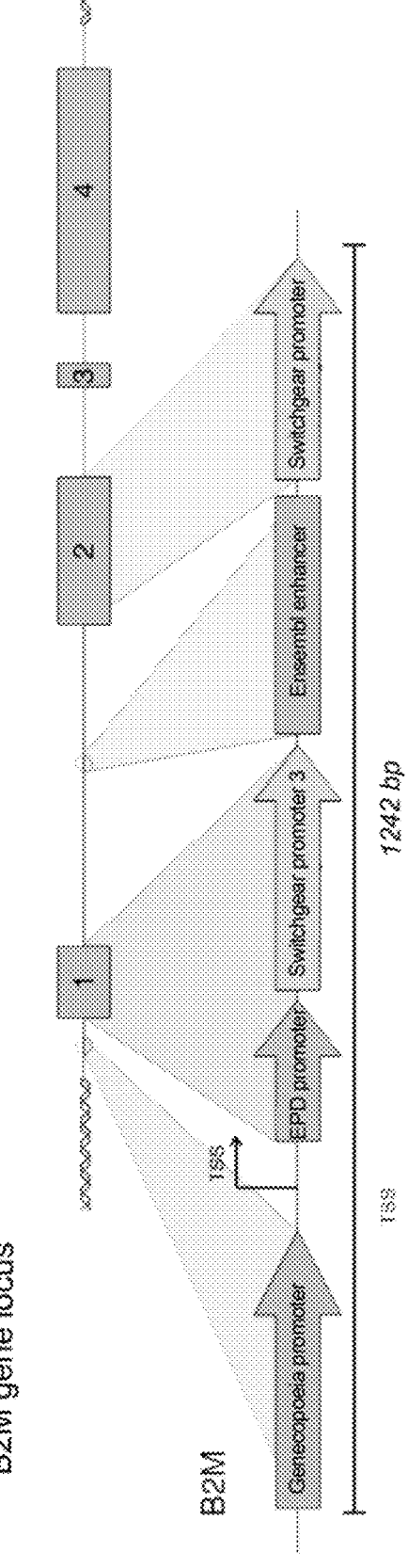
FIG. 1. LV expressing eGFP through two synthetic B2M promoters. A) Two B2M promoters were designed by combining different regulatory regions of human B2M locus as shown in the figure. The complete sequences of both synthetic promoters are shown. As can be seen, the main difference between both constructs is the insertion of the B2M enhancer at the 3'-end (B2M2) or the 5'-end (B2M1) of TSS. B) Diagram of the LV expressing eGFP through synthetic B2M1 and B2M2 promoters. C) Control of the LV expression eGFP through the EF1-alpha promoter. LTR: long terminal repeats; eGFP: enhanced green fluorescent protein; WPRE: woodchuck hepatitis virus (WHP) post-transcriptional regulatory element.

Human primary T-cells were isolated and activated for transduction with lentiviral vectors (LVs) to obtain similar expression levels (~30-50%). The cells were left to stand for 10 days and then stimulated with anti-CD3/CD28 to imitate a physiological stimulation of the TCR/CD3 surface complex. The expression of CD3 and eGFP was evaluated simultaneously at the indicated times at both protein (FACS) and mRNA (non-transduced population) levels divided by said expression at 0 h). C) The Y axis on the left indicates the relative proportion of CD3 mRNA and the Y axis on the right refers to the relative proportion of GFP mRNA expression. Relative ratio=[expression of GFP/expression of GAPDH at TIME]/[expression of GFP/expression of GAPDH at 0 h].

DESCRIPTION OF THE INVENTION

The authors of the present invention have developed a system which allows the expression of CAR following the expression pattern of TCR, preventing high expression levels on the surface of T-cells which have been associated with an inefficient long-term therapy or with harmful, life-threatening side effects, such as a cytokine storm. The authors of the invention have selected LV (lentivirus or lentiviral) as the best system to achieve a stable expression and regulatory regions of the B2M locus as a good candidate for expressing CARs which imitate the expression pattern of TCR following CD3/CD28 stimulation, at both protein and mRNA levels.

Based on the regulatory regions of B2M, the authors of the invention have created two synthetic promoters including most of the regulatory regions of the B2M locus in a reduced size that will allow insertion thereof in an LV backbone.

Therefore, a first aspect of the invention relates to a polynucleotide comprising or consisting of the sequence SEQ ID NO: 1 or 2, hereinafter polynucleotides of the invention, or a polynucleotide comprising or consisting of a sequence having an identity to SEQ ID NO: 1 or 2 of at least:

| | | |
|---|---|---|
| a. | 80% | |
| b. | 85% | |
| c. | 90% | |
| d. | 95% | |
| e. | 99% | |

SEQ ID NO: 1
1161 bp
aattcggcatgcttatcgatttggtccttccttacttgccccctttcggcg gggagcagggggggggtctgggggaggcgtcgcccgggaaagcctgtctg ctgcagcctaaccagggcttttgcgggagcgcatggcttttggctgtaat tcgtgcatttttaacaaaaacgcctgccttctgcgtgagattctccagag caaactgggcggcatgggccctgtggtcttttcgtacacacggcttcctc tttggctctttgcctggttgtttccaacatgtactgtgcctcttactttc ggttttgaaaacatgaggggggttgggcgtggtagcttacgcctgtaatcc cagcacttagggaggccgaggcgggaggatggcttgaggtccgtagttga gaccagcctgggctgctccggtggctgaggcgggaggatctcttgagctt

4

-continued aggcttttgagcagaaagagaaaagaaaagaaagaaagaagtgtgaatac aatctcacaaaatcttgccgccttccctcaatcattttcaataatcccaa cactttgggaggccaaggcaggctgatcactctcaggaactccaaagatt caggtttactcacgtcatccagcagagaatggaaagtcaaatttcctgaa ttgctatgtgtcctcactgttcctcttacaaaagatctgtggactccacc accacgaaatggcggcacctttatttatggtcacagaatgatgtacctaga gggcgctggaagctctaaagccctagcagttactgcttttactattagtg gtcgttttttttctcccccccgccccccgacaaatcaacagaacaaagaaa attacctaaacacttcttaaacatcacgagactctaagaaaaggaaactg aaaacgggaaagtccctctctctaacctggcactgcgtcgctggcttgga gacaggagacggtccctgcgggccttgtcctgattggctgggccgcgttt aatataagtggaggcgtcgcgctgggggcattcctgaagctgacagcatt cgggccgagtgtctcgctccgtggccttagctgtgctcgcgctactctct ctttctggcctggaggctatccagcgagagactctcctaccctcccgctg gcgcgcccgg Specifically, the polynucleotide of the invention of SEQ ID NO 1, also referred to as B2M_EWP1, is a 1161-nucleotide sequence which contains B2 microglobulin (B2M) fragments.

SEQ ID NO: 2
>B2M_EWP2 1264 bp
gaattcggcatgcttatcgattctcactgttcctcttagaaaagatctgt ggactccaccaccacgaaatggggcacctttatttatggtcacacaatgat gtacctagagggcgctggaagctctaaagccctagcagttactgctttta ctattagtggtcgtttttttctcccccccgccccccgacaaatcaacaga acaaagaaaattacctaaacacttcttaaacatcacgagactctaagaaa aggaaactgaaaacgggaaagtccctctctctaacctggcactgcgtcgc tggcttggagacaggagacggtccctgcgggccttgtcctgattggctgg gctcgcgtttaatataagtggaggcgtcgcgctggcgggcattcctgaag cttccctatcagtgatagagatctccctatcagtgatagagagacagcat tcgggccgagtgtctcgctccgtggccttagctgtgctcgcgctactctc tctttctggcctggaggctatccagcgtgagtctctcctaccctcccgct ctggtccttccttacttgcccctttcggcggggagcagggggagggggtctg ggggaggcgtcgcccgggaaagcctgtctgctgcagcctaaccagggctt ttgcgggagcgcatggcttttggctgtaattcgtgcatttttttttaaga aaaacgcctgccttctgcgtgagattctccagagcaaactgggcggcatg ggccctgtggtcttttcgtacacacggcttcctctcttggctctttgcctg gttgtttccaagatgtactgtgcctcttactttcggttttgaaaacatga ggggggtgggcgtggtagcttacgcctgtaatcccagcacttagggaggc cgaggcgggaggatggcttgaggtccgtagttgagaccagcctgggctgc tccggtggctgaggcgggaggatctcttgagcttaggctttttgagcagaa agagaaaagaaagaaagaagtgtgaatacaatctcacaaaatctt

5

-continued

```
gccgccttccctcaatcattttcaataatcccaacactttgggaggccaa ggcaggctgatcactctcaggaactccaaagattcaggtttactcacgtc atccagcagagaatggaaagtcaaatttcctgtggtcttttcgtacagag ggcttcgaattgctatgtgtctgtggtcttttcgtacacagggcttcggc gcgcccgggatcc
```

Specifically, the polynucleotide of the invention of SEQ ID NO 2, also referred to as B2M_EWP2, is a 1264-nucleotide sequence which contains B2 microglobulin (B2M) fragments.

Any of the polynucleotides of the invention (SEQ ID NO 1 or SEQ ID NO 2) are preferably included in lentiviral vectors for the purpose of enabling the stable expression thereof in cells.

To direct the transmembrane polypeptide to the secretory pathway of a host cell, a signal sequence (also known as a leader sequence, prepro sequence, or pre-sequence) can be provided in the sequence of any of the polynucleotides of the invention (SEQ ID NO 1 or SEQ ID NO 2) or in the sequence of a vector, such as a lentiviral vector, comprising said polynucleotides. The secretory signal sequence will be operatively linked to the transmembrane nucleic acid sequence, i.e., the two sequences bind to the correct reading frame and are positioned to direct the newly synthesized polypeptide into the secretory pathway of the host cell. Secretory signal sequences are usually positioned at 5' with respect to the nucleic acid sequence encoding the polypeptide of interest, although certain secretory signal sequences can be positioned in any other part of the nucleic acid sequence of interest (see, for example, Welch et al., U.S. Pat. No. 5,037,743; Holland et al., U.S. Pat. No. 5,143,830). Those skilled in the art will recognize that, in view of genetic code degeneration, a considerable sequence variation is possible among these polynucleotide molecules. Preferably, the sequences of any of the polynucleotides of the invention (SEQ ID NO 1 or SEQ ID NO 2) may comprise optimized codons for expression in mammalian cells, preferably for expression in human cells. Codon optimization refers to the exchange, in a sequence of interest, of codons that are generally rare in highly expressed genes of a given species with codons which are generally common in highly expressed genes of such species, such codons encoding the amino acids like the codons being exchanged.

Therefore, another aspect of the invention relates to a gene construct, hereinafter gene construct of the invention, comprising any of the polynucleotides of the invention (SEQ ID NO 1 or SEQ ID NO 2). Preferably, the gene construct of the invention is a viral vector, and more preferably a lentiviral vector. More preferably, the gene construct of the invention comprises any of the polynucleotides of the invention (SEQ ID NO 1 or SEQ ID NO 2) operatively attached to the sequence of a CAR to drive its expression, wherein the CAR will comprise at least one extracellular ligand-binding domain, a transmembrane domain, and at least one intracellular signaling domain.

Cells of the Invention

Another aspect of the invention relates to a cell, hereinafter cell of the invention, comprising any of the polynucleotides of the invention (SEQ ID NO 1 or SEQ ID NO 2), or the gene construct of the invention which in turn comprises any of the polynucleotides of the invention (SEQ ID NO 1 or SEQ ID NO 2). In a preferred embodiment of this aspect, the cell of the invention is an immune cell. More preferably, populations of cells of the invention are preferred.

In a particular embodiment, the invention relates to a method for the preparation of immune cells for immunotherapy which comprises introducing into said immune cells any of the polynucleotides of the invention (SEQ ID NO 1 or SEQ ID NO 2), or the gene construct or vector according to the present invention, and expanding said cells. In a particular embodiment, the invention relates to a method which comprises providing a cell and expressing at least one CAR on the surface of said cell. In a particular embodiment, the method comprises transforming or transducing the cell with at least any of the polynucleotides of the invention (SEQ ID NO 1 or SEQ ID NO 2) or with a vector or gene construct comprising any of the polynucleotides of the invention (SEQ ID NO 1 or SEQ ID NO 2) operatively attached to the sequence of a CAR, and expressing said polynucleotides in said cell. In other words, preferably, for the cellular transformation or transduction, any of the polynucleotides of the invention (SEQ ID NO 1 or SEQ ID NO 2) is cloned into a vector comprising the CAR of interest.

In another embodiment, said method further comprises a step of genetically modifying said cell by inactivating at least one gene that expresses a component of the TCR, a target for an immunosuppressive agent, the HLA gene, and/or an immune checkpoint gene such as PD1 or CTLA-4. In a preferred embodiment, said gene is selected from the group consisting of TCR-alpha, TCR-beta, CD52, GR, PD1, and CTLA-4. In a preferred embodiment, said method further comprises introducing into said T-cells a rare-cutting endonuclease capable of selectively inactivating said genes by means of DNA cleavage. In a more preferred embodiment, said rare-cutting endonuclease is TALE-nuclease or Cas9 endonuclease.

The different methods described above preferably involve the introduction of CAR into a cell using expression vectors comprising or having the polynucleotides of the invention (SEQ ID NO 1 or SEQ ID NO 2) cloned therein. As a non-limiting example, said CAR can be introduced as transgenes encoded by a lentiviral vector.

Immune Cells

The present invention also relates to isolated cells or cell lines which can be obtained by said method for designing cells. In particular, said isolated cell comprises at least one CAR and a B2 microglobulin promoter, preferably any of the polynucleotides of the invention (SEQ ID NO 1 or SEQ ID NO 2), in particular of SEQ ID NO 1 or 2, operatively attached to CAR to drive its expression. In another embodiment, said isolated cell comprises a population of CARs and promoters of the B2 microglobulin locus, in particular of SEQ ID NO 1 or 2, operatively linked to CARs to drive their expression, each comprising different extracellular ligand-binding domains. Immune cells of the present invention are activated and proliferate independently of the antigen binding mechanisms.

An isolated immune cell, preferably a T-cell obtained according to any of the methods described above, is also included in the scope of the present invention. Said immune cell refers to a cell of hematopoietic origin functionally involved in initiating and/or carrying out an innate and/or adaptive immune response. Said immune cell according to the present invention can derive from a stem cell. The stem cells can be adult stem cells, non-human embryonic stem cells, more particularly non-human stem cells, umbilical cord stem cells, progenitor cells, bone marrow stem cells, induced pluripotent stem cells, totipotent stem cells, or hematopoietic stem cells. Representative human cells are CD34+ cells. Said isolated cell also can be a dendritic cell, a killer dendritic cell, a mast cell, an NK cell, a B-cell, or a T-cell. In a preferred embodiment, it is a T-cell selected from the group consisting of inflammatory T lymphocytes, cytotoxic T lymphocytes, regulatory T lymphocytes, or helper T lymphocytes. In another embodiment, said cell can derive from the group consisting of CD4+T lymphocytes and CD8+T lymphocytes. Before expanding and genetically modifying the cells of the invention, a cell source can be obtained from a subject through a variety of methods. The cells can be obtained from a series of non-limiting sources, including peripheral blood mononuclear cells, bone marrow, tissue of lymph nodes, umbilical cord blood, tissue of the thymus, tissue of an infection site, ascites, pleural effusion, tissue of the spleen and tumors. In certain embodiments of the present invention, any number of T-cell lines available to and known by those skilled in the art can be used. In another embodiment, said cell can derive from a healthy donor, a patient diagnosed with cancer, or a patient diagnosed with infection. In another embodiment, said cell is part of a mixed population of cells having different phenotype characteristics. The scope of the present invention also encompasses a cell line obtained from a T-cell transformed according to the method described above. Modified cells which are resistant to an immunosuppressive treatment and can be obtained using the preceding method are encompassed in the scope of the present invention.

T-Cell Activation and Expansion

Either before or after the generation of transformed or transduced T-cells, even if the modified immune cells of the present invention are activated and proliferate independently of the antigen-binding mechanisms, the immune cells, particularly the T-cells of the present invention, can be additionally activated and expanded generally using methods such as those described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and the US patent application with publication no. 20060121005. The T-cells can be expanded in vitro or in vivo. Generally, the T-cells of the invention are expanded through contact with an agent that stimulates a CD3/TCR complex and a co-stimulatory molecule on the surface of T-cells to create an activation signal for the T-cells. For example, chemicals such as calcium ionophore A23187, phorbol 12-myristate 13-acetate (PMA), or mitogenic lectins such as phytohemagglutinin (PHA), can be used to create an activation signal for the T-cell.

As non-limiting examples, the populations of T-cells can be stimulated in vitro, by contact with an anti-CD3 antibody, or an antigen-binding fragment thereof, or an anti-CD2 antibody immobilized on a surface, or by contact with a protein kinase C activator (for example, bryostatin) together with calcium ionophore. For the co-stimulation of an accessory molecule on the surface of T-cells, a ligand which binds to the accessory molecule is used. For example, a population of T-cells can be contacted with an anti-CD3 antibody and an anti-CD28 antibody under conditions suitable for stimulating T-cell proliferation. Conditions suitable for culturing T-cells include a suitable medium (for example, minimum essential medium or RPM11640 medium, or X-vivo 5 (Lonza)) which may contain factors required for proliferation and viability, including serum (for example, human or fetal bovine serum), interleukin-2 (IL-2), insulin, IFN-g, 1L-4, 1L-7, GM-CSF, -10, -2, 1L-15, TGF, and TNF- or any other cell growth additive. Other cell growth additives include, but are not limited to, surfactant, plasmanate, and reducing agents such as N-acetylcysteine and 2-mercaptoethanol. The media can include RPMI 1640, A1M-V, DMEM, MEM, a-MEM, F-12, X-Vivo 1, and X-Vivo 20, Optimizer, with added amino acids, sodium pyruvate, and vitamins, either without serum or supplemented with a suitable amount of serum (or plasma) or a defined set of hormones, and/or an amount of cytokines sufficient for T-cell growth and expansion. Antibiotics, for example, penicillin and streptomycin, are also included in experimental cultures, not in cell cultures that will be infused into a subject. Target cells are kept under conditions required to support growth, for example, at a suitable temperature (for example, 37° C.) and atmosphere (for example, air plus 5% $CO_2$). T-cells which have been exposed to several stimulation times may exhibit different characteristics.

In another particular embodiment, said cells can be expanded by means of co-culture with tissue or cells. Said cells also can be expanded in vivo, for example, in the blood of the subject after administering said cell to the subject.

Compositions of the Invention

Another aspect of the invention relates to a composition, hereinafter composition of the invention, comprising any of the polynucleotides of the invention (SEQ ID NO 1 or SEQ ID NO 2), the gene construct of the invention comprising any of the polynucleotides of the invention (SEQ ID NO 1 or SEQ ID NO 2), or the cell of the invention. In a preferred embodiment, the composition of the invention further comprises a pharmaceutically acceptable vehicle. In another preferred embodiment, the composition of the invention is a pharmaceutical composition. In another preferred embodiment, the composition of the invention comprises one or more additional active ingredients.

Medical Uses of the Invention

Another aspect of the invention relates to any of the polynucleotides of the invention (SEQ ID NO 1 or SEQ ID NO 2), the gene construct of the invention, the cell of the invention, or the composition of the invention, for use thereof in therapy.

Another aspect of the invention relates to any of the polynucleotides of the invention (SEQ ID NO 1 or SEQ ID NO 2), the gene construct of the invention, the cell of the invention, or the composition of the invention, for the treatment of cancer. In a preferred embodiment, the cancer is selected from the list consisting of neoplasms, B-cell neoplasms, lymphoma, leukemia, and/or myeloma.

The isolated cells obtained by the different methods or the cell line derived from said isolated cell as described above can be used as a medication. In another embodiment, said medication can be used for the treatment of cancer, particularly for the treatment of B-cell lymphomas and leukemia in a patient in need thereof. In another embodiment, said isolated cell according to the invention or cell line derived from said isolated cell can be used in the manufacturing of a medication for the treatment of cancer in a patient in need thereof.

In another aspect, the present invention is based on methods for treating patients in need thereof, said method comprising at least one of the following steps:

(a) providing any of the polynucleotides of the invention (SEQ ID NO 1 or SEQ ID NO 2), the gene construct of the invention, the cell of the invention, or the composition of the invention, and preferably an immune cell obtainable by means of any of the methods described above;

(b) Administering any of the polynucleotides of the invention (SEQ ID NO 1 or SEQ ID NO 2), the gene construct of the invention, the cell of the invention, or the composition of the invention, or more preferably transformed immune cells, to said patient.

In one embodiment, said T-cells of the invention can undergo an in vivo solid T-cell expansion and can persist for a prolonged period of time.

Said treatment can be palliative, curative, or prophylactic. It can be part of an autologous immunotherapy or part of an allogenic immunotherapy treatment. Autologous means that the cells, the cell line, or the population of cells used for treating patients originate from said patient. Allogenic is understood to mean that the cells or the population of cells used for treating patients do not originate from said patient, but rather from a donor.

Cells which can be used with the described methods are described in the preceding section. The treatment can be used to treat patients diagnosed with cancer. Cancers which can be treated may comprise non-solid tumors (such as blood tumors, including, among others, pre-B ALL (pediatric indication), adult ALL, mantle cell lymphoma, diffuse large B-cell lymphoma, and the like). Types of cancers to be treated with CARs of the invention include, but are not limited to, certain lymphoid neoplasms or leukemias. Adult tumors/cancers and childhood tumors/cancers are also included. It can be a treatment in combination with one or more cancer therapies selected from the group of antibody therapy, chemotherapy, cytokine therapy, dendritic cell therapy, gene therapy, hormone therapy, laser light therapy, and radiotherapy.

According to a preferred embodiment of the invention, said treatment can be administered to patients subjected to an immunosuppressive treatment. In fact, the present invention is preferably based on cells or a population of cells, which have been made resistant to at least one immunosuppressive agent due to the inactivation of a gene encoding a receptor for such immunosuppressive agent. In this aspect, the immunosuppressive treatment must help in the selection and expansion of T-cells according to the invention inside the patient.

The cells or population of cells according to the present invention can be administered in any convenient manner, even by means of aerosol inhalation, injection, ingestion, transfusion, implantation, or transplant. The compositions described herein can be administered to a patient subcutaneously, intradermally, intratumorally, intranodally, by intramedullary injection, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells/kg body weight, preferably $10^5$ to $10^6$ cells/kg body weight, including all the integer values of numbers of cells within those ranges. The cells or population of cells can be administered in one or more doses. In another embodiment, said effective amount of cells is administered as a single dose. In another embodiment, said effective amount of cells is administered as more than one dose for a period of time. The time of administration is at the discretion of the attending physician and depends on the clinical condition of the patient. The cells or population of cells can be obtained from any source, such as blood, banks, or a donor, including the patient him/herself. Although individual needs vary, determination of the optimal ranges of the effective amounts of a given type of cell for a particular disease or conditions is within the knowledge of the skilled person.

An effective amount means an amount which provides a therapeutic or prophylactic benefit.

The administered dose will depend on the age, health, and weight of the intended patient, type of concurrent treatment, if any, the frequency of treatment, and the nature of the desired effect. In another embodiment, said effective amount of cells or a composition comprising those cells is administered parenterally. Said administration can be an intravenous administration. Said administration can be performed directly by means of injection into a tumor.

In certain embodiments of the present invention, the cells are administered to a patient together with (for example, before, simultaneously, or after) any number of forms of treatment including, among others, treatment with agents such as antiviral, cidofovir and interleukin-2, cytarabine (also known as ARA-C), or nataliziimab therapy, treatment for MS patients, or efaliztimab treatment for psoriasis patients, or other treatments for PML patients. In other embodiments, the T-cells of the invention can be used in combination with chemotherapy, radiation, immunosuppressive agents, such as cyclosporin, azathioprine, methotrexate, mycophenolate and FK506, antibodies or other immunoablative agents such as CAM PATH, anti-CD3 antibodies, or other antibody, cytoxin, fludaribine, cyclosporin, FK506, rapamycin, mycoplienolic acid, steroid, FR901228, cytokine, and irradiation therapies. These drugs inhibit calcium-calcineurin dependent phosphatase (cyclosporin and FK506) or inhibit p70S6 kinase which is important for factor (rapamycin)-induced signaling growth (Henderson, Naya et al. 1991; Liu, Albers et al. 1992; Bierer, Hollander et. al. 1993). In an additional embodiment, the cell compositions of the present invention are administered to a patient together with (for example, before, simultaneously, or after) a bone marrow transplant, ablative T-cell therapy using chemotherapy agents such as fludarabine, external beam radiotherapy (XRT), cyclophosphamide, or antibodies such as OKT3 or CAMPATH. In another embodiment, the cell compositions of the present invention are administered after an ablative B-cell therapy, such as agents which react with CD20, for example, Rituxan. For example, in one embodiment, the subjects can be subjected to a standard high-dose chemotherapy treatment followed by a peripheral blood stem cell transplant. In certain embodiments, the subjects receive an infusion of expanded immune cells of the present invention after transplant. In an additional embodiment, the expanded cells are administered before or after surgery.

Other definitions

Unless otherwise specified, "a", "an", "the", and "at least one" are used interchangeably and means one or more than one.

Amino acid residues in a polypeptide sequence are herein designated according to the one-letter code in which, for example, Q means Gln or a glutamine residue, R means Arg or an arginine residue, and D means Asp or an aspartic acid residue.

Amino acid substitution means the substitution of an amino acid residue with another, for example, the replacement of an arginine residue with a glutamine residue in a peptide sequence is an amino acid substitution.

Nucleotides are designated as follows: the one-letter code is used to designate the base of a nucleoside: a is adenine, t is thymine, c is cytosine, and g is guanine. For degenerated nucleotides, r represents g or a (purine nucleotides), k represents g or t, s represents g or c, w represents a or t, m represents a or c, y represents t or c (pyrimidine nucleotides), d represents g, a, or t, v represents g, a, or, c, b represents g, t, or c, h represents a, t, or c, and n represents g, a, t, or c.

As it is used herein, "nucleic acid" or "polynucleotides" refer to nucleotides and/or polynucleotides, such as desoxy-ribonucleic acid (DNA) or ribonucleic acid (RNA), oligo-nucleotides, fragments generated by polymerase chain reaction (PCR), and fragments generated by ligation, cleavage, endonuclease action, and exonuclease action. Nucleic acid molecules can be made up of monomers which are naturally occurring nucleotides (such as DNA and RNA) or natural nucleotide analogs (e.g., enantiomeric forms of natural nucleotides) or a combination of both. Modified nucleotides can have alterations in sugar and/or pyrimidine or purine base moieties. Sugar modifications include, for example, the replacement of one or more hydroxyl groups with halogens, alkyl groups, amines, and azide groups, or sugars can be functionalized as ethers or esters. Furthermore, the entire sugar fraction can be replaced with sterically and electronically similar structures, such as aza sugars and carbocyclic sugar analogs. Examples of modifications in a base moiety included alkylated purines and pyrimidines, acylated purines or pyrimidines, or other well-known heterocyclic substitutes. Nucleic acid monomers can be attached by means of phosphodiester bonds or analogs of said bonds. Nucleic acids can be single stranded or double stranded.

Chimeric antigen receptor (CAR) is understood to mean molecules which combine a binding domain for a component present in the target cell, for example, an antibody-based specificity for a desired antigen (for example, tumor antigen), with a T-cell receptor which activates the intracellular domain receptor for generating a chimeric protein that exhibits a specific anti-target cellular immunity. Generally, CAR consists of a single-stranded extracellular antibody (scFv) fused to the intracellular signaling domain of the zeta chain of the T-cell antigen receptor (scFv) complex and, when expressed in T-cells, is capable of redirecting antigen recognition based on monoclonal antibody specificity.

"Delivery vector" or "delivery vectors" is understood to mean any delivery vector which can be used in the present invention for placing in cellular contact (i.e., "contacting") or releasing (i.e., "introducing") chemical agents/substances and molecules (proteins or nucleic acids) required in the present invention into cells or subcellular compartments. It includes, but is not limited to, liposomal release vectors, viral release vectors, drug release vectors, chemical carriers, polymeric carriers, lipoplexes, polyplexes, dendrimers, microbubbles (ultrasound contrast agents), nanoparticles, emulsions, or other suitable transfer vectors. These release vectors allow supplying molecules, chemicals, macromolecules (genes, proteins), or other vectors such as plasmids, peptides. In these cases, the administration vectors are molecule carriers. "Release vector" or "release vectors" is also understood to mean the release methods intended for performing transfection.

The terms "vector" or "vectors" refer to a nucleic acid molecule capable of transporting another nucleic acid to which it is linked. A "vector" in the present invention includes, but is not limited to, a viral vector, a plasmid, an RNA vector, or a linear or circular DNA or RNA molecule which can consists of a chromosomal molecule, a non-chromosomal molecule, a semi-synthetic molecule, or synthetic nucleic acids. Preferred vectors are those capable of autonomous replication (episomal vector) and/or expression of the nucleic acids to which they are linked (expression vectors). A large number of suitable and commercially available vectors are known to those skilled in the art.

Viral vectors include retrovirus, adenovirus, parvovirus (e.g., adeno-associated viruses), coronavirus, negative-strand RNA viruses such as orthomyxovirus (e.g., influenza virus), rhabdovirus (e.g., rabies and vesicular stomatitis virus), paramyxovirus (e.g., measles and Sendai), positive-strand RNA viruses such as picornavirus and alphavirus, and double-stranded DNA viruses including adenovirus, herpes-virus (e.g., herpes simplex virus types 1 and 2, Epstein-Barr virus, cytomegalovirus), and poxvirus (e.g., vaccinia, fowl-pox, and canarypox). Other viruses include Norwalk virus, togavirus, flavivirus, reovirus, papovirus, hepadnavirus, and hepatitis virus, for example. Examples of retroviruses include: avian sarcoma leukosis, mammalian type C virus, type B virus, type D virus, HTLVBLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

"Lentiviral vector" is understood to mean HIV-based lentiviral vectors that are very promising for release due to their relatively large packaging capacity, reduced immunogenicity, and their ability to stably transduce a large range of different cell types with high efficiency. Lentiviral vectors are typically generated following transient transfection of three (packaging, envelope, and transfer) or more plasmids into producer cells. Like HIV, lentiviral vectors enter the target cell through the interaction of viral surface glycoproteins with receptors on the cell surface. On entry, the viral RNA is subjected to reverse transcription, which is mediated by the viral reverse transcriptase complex. The product of reverse transcription is a double-stranded linear viral DNA, which is the substrate for viral integration in the DNA of infected cells. "Integrative lentiviral vectors (or LVs)" are understood to mean vectors such as, for example, but without limitation, those that are capable of integrating the genome of a target cell. In contrast, "non integrative lentiviral vectors (or NILVs)" refer to efficient gene delivery vectors that do not integrate the genome of a target cell by means of the action of the virus integrase.

The vectors and release vectors can be associated or combined with one another using any cell permeabilization techniques, such as sonoporation or electroporation or derivatives of these techniques.

Cell or cells is understood to mean any eukaryotic living cell, primary cell, and cell line derived from these organisms for in vitro cultures.

"Primary cell" or "primary cells" is understood to mean cells that are extracted directly from living tissue (i.e., biopsy material) and established for growth in vitro, that have undergone very few population doublings, and are therefore more representative of the main components and characteristics of the tissues from which they are derived, in comparison to continuous tumorigenic or artificially immortalized cell lines.

As non-limiting examples, cell lines from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Muda 4 cells can be selected.

All these cell lines can be modified by means of the method of the present invention to provide cell line models to produce, express, quantify, detect, study a gene or a protein of interest; these models can also be used to select biologically active molecules of interest in research and production and in various fields such as chemistry, biofuels, therapeutics, and agronomy, as non-limiting examples.

"Mutation" is understood to mean the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. Mutation can affect the coding sequence of a gene or its regulatory sequence. It can also affect the structure of the genomic sequence or the structure/stability of the encoded mRNA.

"Variant(s)" is understood to mean a repeat variant, a variant, a DNA-binding variant, a TALE nuclease variant, a polypeptide variant obtained by mutation or replacement of at least one residue in the amino acid sequence of the parent molecule.

"Functional variant" is understood to mean a catalytically active mutant of a protein or a protein domain; said mutant may have the same activity compared to its parent protein or protein domain or additional properties, or higher or lower activity.

"Identity" refers to sequence identity between two nucleic acid molecules or polypeptides. Identity can be determined by means of comparing a position in each sequence which may be aligned for comparison purposes. When a position in the compared sequence is occupied by the same base, then the molecules are identical at that position. A degree of similarity or identity between nucleic acid or amino acid sequences is based on the number of identical or matching nucleotides at positions shared by the nucleic acid sequences. Various alignment algorithms and/or programs can be used to calculate the identity between two sequences, including FASTA or BLAST, which are available as part of the GCG sequence analysis package (University of Wisconsin, Madison, Wis.), and can be used, for example, with the predetermined configuration. For example, polypeptides having at least 70%, 85%, 90%, 95%, 98%, or 99% identity to the specific polypeptides described herein and preferably exhibiting substantially the same functions, as well as the polynucleotide encoding such polypeptides, are contemplated "Similarity" describes the relationship between the amino acid sequences of two or more polypeptides. BLASTP can also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62. or BLOSUM80. Unless otherwise indicated, a similarity score will be based on the use of BLOSUM62. When BLASTP is used, the percentage of similarity is based on the BLASTP positive score and the percentage of sequence identity is based on the BLASTP identity score. BLASTP "identities" shows the number and fraction of total residues in the high scoring sequence pairs which are identical; and BLASTP "positives" shows the number and fraction of residues for which the alignment scores have positive values and are similar to one another. Amino acid sequences having these degrees of identity or similarity or any intermediate degree of identity or similarity to the amino acid sequences described herein are contemplated and encompassed by this disclosure. The polynucleotide sequences of similar polypeptides are deduced using the genetic code and can be obtained by conventional means. The polynucleotide encoding a functional variant of this type would be produced by reverse translating its amino acid sequence using the genetic code.

"Signal-transducing domain" or "co-stimulatory ligand" refers to a molecule in an antigen presenting cell that binds specifically to an analogous co-stimulatory molecule in a T-cell, providing a signal which, in addition to the primary signal provided, for example, by means of the binding of a TCR/CD3 complex with an MHC molecule loaded with peptide, mediates a T-cell response including, but without limitation, proliferation activation, differentiation, and the like. The co-stimulatory ligand can include, among others, CD7, B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, M1CB, HVEM, lymphotoxin beta receptor, 3/TR6, ILT3, ILT4, a Toll ligand receptor-binding agonist or antibody, and a ligand binding specifically to B7-H3. A co-stimulatory ligand also encompasses, among others, an antibody binding specifically to a co-stimulatory molecule present in a T-cell such as, but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand binding specifically to CD83.

A "co-stimulatory molecule" refers to the cognate binding partner in a T-cell that binds specifically to a co-stimulatory ligand, thereby mediating a co-stimulatory response of the cell such as, but not limited to, proliferation. Co-stimulatory molecules include, but are not limited to, an MHC class I molecule, BTLA, and Toll ligand receptor.

As it is used herein, a "co-stimulatory signal" refers to a signal which, in combination with primary signal, such as TCR/CD3 ligation, leads to T-cell proliferation and/or upregulation or downregulation of key molecules.

As it is used herein, the term "extracellular ligand-binding domain" is defined as an oligo- or polypeptide which is capable of binding to a ligand. Preferably, the domain will be capable of interacting with a cell surface molecule. For example, the extracellular ligand-binding domain can be chosen to recognize a ligand that acts as a cell surface marker in target cells associated with a particular disease state. In that sense, examples of cell surface markers that can act as ligands include those associated with viruses, bacteria, and parasitic infections, autoimmune diseases, and cancer cells.

As it used herein, the term "subject" or "patient" includes all members of the animal kingdom, including non-human primates and humans.

The preceding description of the invention allows any person skilled in the art to make and use the invention, particularly for the object of the attached claims, which are part of the original description.

Where a numerical limit or range is indicated herein, the endpoints are included. Furthermore, all values and subranges within a numerical limit or range are specifically included as if they were explicitly stated.

Various modifications to the preferred embodiments will be readily apparent to those skilled in the art, and the generic principles defined herein may be applied to other embodiments and applications without departing from the spirit and scope of the invention. Therefore, this invention is not intended to be limited to the embodiments that are shown but is to be accorded the widest scope according to the principles and features described herein.

Having generally described this invention, a further understanding can be obtained by reference to certain specific examples which are provided herein solely for illustration purposes and are not intended to be limiting unless otherwise specified.

Unless specifically defined herein, all technical and scientific terms used have the same meaning as commonly understood by one skilled in the fields of gene therapy, biochemistry, genetics, and molecular biology. All methods and materials that are similar or equivalent to those described herein can be used in the practice or testing of the present invention, with suitable methods and materials being described herein. All publications, patent applications, patents, and other references mentioned herein are incorporated by reference in their entirety. In case of a dispute, the present specification, including definitions, will prevail. Furthermore, the materials, methods, and examples are solely illustrative and are not intended to be limiting, unless otherwise specified. Unless otherwise indicated, the practice of the present invention will use conventional cell biology, cell culture, molecular biology, transgenic biology, microbiology, recombinant DNA, and immunology techniques, which are within the knowledge of the skilled person. Such techniques are explained fully in the literature. See, for example, Current Protocols in Molecular Biology (Frederick M. AUSUBEL, 2000, Wiley and Sons Inc, Library of Congress, USA); Molecular Cloning: A Laboratory Manual, Third Edition, (Sambrook et. al., 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames& S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds. -in-chief, Academic Press, Inc., New York), specifically, Vols. 154 and 155 (Wu et. al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Examples of the Invention

Outline

1. In-silico generation of chimeric promoters of the different molecules involved in the TCR signaling pathway.
   a. Selection of molecules involved in the TCR signaling pathway.
   b. Database search of regulatory elements involved in the expression and promoter function of the selected molecules.
   c. Design of final constructs in silico.
2. Generation of eGFP+ T-cells, where eGFP is expressed under the control of different chimeric promoters.

a. Cloning of promoter sequences into a lentiviral vector with GFP.
   b. Production of lentiviral vectors with different constructs.
   c. Cell transduction with viral vectors and study of GFP expression kinetics at both mRNA and protein levels.
3. Generation of CAR-CD19 T-cells, where CAR is expressed under the control of different chimeric promoters.
   a. Cloning of promoter sequences into a CAR-containing lentiviral backbone.
   b. Production of lentiviral vectors with different constructs.
   c. Cell transduction with viral vectors and study of CAR expression kinetics at both mRNA and protein levels.

Materials and Methods

1. Design of Chimeric Promoters

A construct (B2M) containing a promoter defined by Genecopoeia (chr15:45002449-45003706) was generated. A promoter defined by EPD (chr15:45003666-45003725) and promoter 3 defined by Switchgear were also added downstream. These two promoters partially overlap exon 1 of B2M. A region defined by Ensembl as enhancer (chr15: 45004699-45004998) was placed downstream, and another promoter defined by Switchgear which overlaps exon 2 was placed in the 3' region. The B2M TetO construct is identical, but with the TetO sequence being placed downstream of TSS, whereas in the B2M Enh5' construct, the position of the enhancer defined by Ensembl was changed from the 3' region to the 5' region.

2. Molecular Cloning of Vectors

The constructs were reconstituted in 20 μL of water of ultrapure water under sterility conditions.

a. SEWP Plasmid with Chimeric Promoters

SEWP is a plasmid which allows the expression of eGFP under the control of SFFV (spleen focus-forming virus) viral promoter. This plasmid (available in the laboratory) was modified to substitute the promoter with chimeric constructs. Combined digestions of all the constructs were performed with BamHI and EcoRI restriction enzymes (New England Biolabs) using buffer 2.1 (New England Biolabs) for 1.5 hours at 37° C. Ultrapure agarose gel electrophoresis was performed and bands were isolated by means of the QIAquick® Gel Extraction Kit (QIAGEN). At the same time, the SEWP backbone was digested with the same enzymes to obtain the promoter-free fragment. The promoters were ligated with the SEWP fragments using T4 DNA ligase (New England Biolabs) in an insert:vector ratio of 7:1. The reaction was carried out overnight at 16° C. Competent *E. coli* Stbl3 bacteria (Life Technologies) were transformed with the ligation product, and positive colonies were confirmed by means of a colony PCR, with the following program: 1× (95° C., 10 minutes); 35× (95° C., 30 seconds/62° C., 30 seconds/72° C., 30 seconds); 1× (72° C., 10 minutes), by means of the KAPA Taq PCR kit (Kapa Biosystems) and the following primers (Sigma): Fw-cPPT (5'-ACAGCAGAGATCCAGTTTGG-3') and Rv-eGFP (5'-TCACTCTCGGCATGGACG-3') (FIG. 5). A miniprep using the Wizard® Plus SV Minipreps DNA Purification System kit (Promega) was performed for ligation-positive colonies, and plasmid DNA was checked by means of HindIII pattern and sequencing.

b. CAR 3G with Chimeric Promoters

The plasmids of interest were generated from a third-generation anti-CD19 CAR (Creative Biolabs) having the EF1-α (Elongation factor 1-α) promoter. Four constructs, i.e., CD247, LCK, B2M, and CD4 P1, were cloned into the lentiviral backbone of CAR. To that end, digestions with ClaI and EcoRI enzymes and buffer 3.1 (New England Biolabs) were performed on the original plasmid of CAR to release the promoter and on the constructs in pUC57 to obtain the chimeric promoters, at 37° C. for 1.5 hours. Bands were isolated from an ultrapure agarose gel and ligation was similarly performed. Competent bacteria were transformed and positive colonies were again confirmed by means of a colony PCR with primers Fw cPPT-clinical (5'-GTGCAGGGGAAAGAATAGTAG-3') and Rv CD19 (5'-TACAGGACTTTCTTTCTGCC-3'). Minipreps for positive colonies were performed with the same kit, and checked by means of HindIII pattern and sequencing.

3. Cell Culture a. Cell Line Culture

Four cell lines were cultured. The cell line used for the production of lentiviral vectors was HEK-293T (human embryonic kidney cells, ATCC® CRL-11268TH). These are adherent cells which were cultured in T175 flasks with DMEM (Dulbecco's Modified Eagle Medium) medium (Biowest) complemented with 10% fetal bovine serum (FBS) (Gibco) and 1% penicillin/streptomycin (P/S; 0.5% each) (Biowest). The BxPC-3 line (human pancreatic adeno-carcinoma cells, ATCC® CRL1687™) is also an adherent cell line which was cultured in T25 flasks with RPMI-1640 (Roswell Park Memorial Institute) medium (Biowest) complemented with 10% FBS and 1% P/S. The Jurkat line (acute T-cell leukemia cell line, ATCC® TIB-152™) and Namalwa line (Burkitt lymphoma cell line, ATCC® CRL-1432™) are suspended cells which are also cultured with RPMI-1640 medium complemented with 10% FBS and 1% P/S, both cultured in T25 flasks.

The four cell lines were kept in incubators at a temperature of 37° C. HEK-293T was kept in an atmosphere with 10% carbon dioxide ($CO_2$), whereas the 3 remaining lines were kept in an atmosphere with 5% $CO_2$. The cells were subjected to passage 3 times a week, maintaining a cell density of about $1*10^6$ cells/m L.

b. Culture of Primary T-Cells

Primary T-cells were obtained from the mobilized peripheral blood of a healthy donor. Peripheral blood mononuclear cells (PBMCs) were isolated from the peripheral blood by means density gradient centrifugation using, to that end, Lymphosep (Biowest), a medium specific for separating lymphocytes. Centrifugation was carried out for 30 minutes at 400 g without stopping or acceleration. Successive washings were performed, and T lymphocytes were isolated from the cell cocktail using the MACSxpress® Pan T Cell Isolation kit (Miltenyi Biotec), consisting of a mixture of magnetic microsphere-conjugated antibodies targeting most PBMC surface markers with the exception of CD3, so it constitutes a magnetic separation method based on the negative depletion of all cell types with the exception of T-cells (CD3+). Isolated T-cells were cultured with Tex-MACS™ medium (Miltenyi Biotec), a medium specific for T-cells, complemented with 5% human AB serum (Biowest), 1% P/S, and 20 IU/mL of interleukin-2 (IL-2) (Miltenyi Biotec), kept in an incubator at 37° C. and 5% $CO_2$. To favor cell growth, T-cells were stimulated through TCR with T cell TransAct™ (Miltenyi Biotec), a polymeric anti-CD3/anti-CD28 nanomatrix. The cells were subjected to passage between 2 and 3 times a week, maintaining a cell density of $1*10^6$ cells/mL.

4. Production of Lentiviral Vectors

Vectors were produced using HEK-293T cells as packaging cells. The cells were seeded into 6-well plates (Life Sciences) with a confluence of more than 90%.

a. Transfection

A second-generation packaging system, which involves the use of 3 lentiviral genome-derived plasmids: 1) Transfer plasmid (B2M-SEWP and B2M-CAR); 2) Packaging plasmid (pCMV8.9) of the HIV virus, and 3) Envelope plasmid (pMD2.G) VSV-G, having the greatest range of infectivity, was used. The ratio of 10:7:3, respectively, was maintained between said plasmids. The chosen transfectant agent was LipoD293™ (SigmaGen Laboratories). Transfection was performed in serum-free DMEM and a medium change was performed with Optimen (Gibco) 5 hours post-transfection to eliminate the long-term toxicity of VSV-G and facilitate subsequent concentration.

b. Collection of Viral Supernatant and Concentration

Three collections were performed, with the first collection being performed 24 hours, the second collection 48 hours, and the third collection 72 hours post-transfection. Viral particles present in the supernatant were collected using sterile 5 mL syringes (Terumo) and filtered using filters with a pore size of 0.45 μm (Life Sciences). Viral particles were concentrated using 100 kD Amicon Ultra-15 filters (Millipore) by means of centrifugation at 1800 g at 4° C. The vectors were stored at −80° C.

c. Titration

Vector titration (transduction units/milliliter; TU/mL) was performed by calculating efficient particles by means of flow cytometry (FACS Canto II, BD Biosciences).

5. Cell Transduction

In the case of GFP vectors, transduction of 5 cell types was performed: Jurkat, Namalwa, HEK-293T, BxPC-3, and primary T-cells. With respect to Jurkat and Namalwa cells, 100,000 cells were plated per well in 48-well plates and viral vectors were added. To improve transduction efficiency, the cells were subjected to spinoculation. Spinoculation is a centrifugation process at 800 g, 32° C., for 1 hour to favor cell—vector contact. In the case of 293T cells, 100,000 cells were also plated. With respect to BxPC-3 cells, 50,000 cells were plated per well in a 24-well plate. Finally, in the case of T-cells, 200,000 cells were plated per well in 96-well plates and activated before transduction through TCR using T-cell TransAct™ for 24 hours. Transduction was performed by means of spinoculation. In all the cases, a medium change was performed 5 hours post-transduction and the percentage of transduced T-cells was determined 3 days later by means of flow cytometry.

In the case of CAR vectors, transduction was carried out in Jurkat cells and primary T-cells following the same method.

6. RT-PCR

This technique was performed using about 700,000 T-cells from which messenger RNA was extracted with Trizol (Ambion). Once obtained, reverse transcription of the messenger RNA was carried out by putting the same amount of mRNA in all the samples. Thereafter, the complementary DNA (cDNA) was diluted, and real-time PCR of all the samples was carried out in duplicate using the primers attached in Table 1.

TABLE 1

| Primers used for RT-PCR. | Sequence (5' → 3') |
|---|---|
| Fw GFP | AAGCTGACCCTGAAGTTCAT |
| Rev GFP | CGTCGTCCTTGAAGAAGAT |
| Fw CD3 | AAGATGAAGTGGAAGGCG |
| Rev CD3 | CTCAGGAACAAGGCAGTG |
| Fw CD4 | AGAAAGACGCAAGCCCAG |
| Rev CD4 | GCAGCACCAGAAGCAAGT |
| Fw GAPDH | ATGGGGAAGGTGAAGGTCG |
| Rev GAPDH | GGGGTCATTGATGGCAACAATA |

7. Flow Cytometry

For flow cytometry experiments, between 20,000 and 50,000 cells were stained with different antibodies which are attached in Table 2.

TABLE 2

| Antibodies used before flow cytometry reading. | | | | |
|---|---|---|---|---|
| Target antibody | Fluorochrome | Use | Concentration | Company |
| CD3 | PerCP-Cy5.5 | T-cell marker | 1:100 | eBiosciences |
| CD8 | APC | T-cell subpopulation marker | 1:100 | eBiosciences |
| CD45RA | PE | T-cell phenotype | 1:100 | eBiosciences |
| CD62L | PE-Cy7 | T-cell phenotype | 1:100 | eBiosciences |
| EGFRt | PE | CAR identification | 1:50 | Biolegend |

8. Statistical Data Analysis

Statistical data analysis was carried out using GraphPad Prism 6, using mean, standard deviation associated with the mean (SEM), and a two-tailed unpaired Student's t-test with a significance *** for $p<0.001$.

Results

In Silico Design of Chimeric Promoters

The first step to achieve the present invention was to design promoters that would be used subsequently for regulating the expression of eGFP and CAR.

It has been observed that β-2 microglobulin (B2M) may exhibit an expression pattern similar to that of TCR. B2M is a structural protein of class I major histocompatibility complex (MHC) that is present in all nucleated cells. Its presence is fundamental for a stable antigen binding to this complex, while its absence causes the inability of CD8+ T-cells to develop.

B2M-derived promoters differ from one another in terms of the presence or absence of the TetO region, as well as the position of the enhancer defined by Ensembl.

Thereafter, the promoters were cloned into lentiviral GFP backbones and the constructs were selected for cloning into CAR-containing lentiviral backbones (FIG. 1A).

Generation of GFP+ T-Cells with Chimeric Promoters

Once the promoters of the invention were cloned into a lentiviral GFP+ backbone, lentiviral vectors were generated to enable transducing primary T-cells, which will allow generating T-cells that express the eGFP reporter gene under each of the previously designed promoters.

Lentiviral vectors were generated following the method explained above, and the titer of the vectors of the invention was calculated in a step prior to T-cell transduction. Once the viral vectors of the invention have been titrated, the same process is followed to transduce primary T-cells previously isolated from a population of T-cells (CD3+) greater than 70%.

B2M Mimics the Expression Pattern of TCR

To study the expression of GFP under the control of B2M-derived promoters, both the protein and the messenger RNA were studied. In that sense, GFP and CD3 messenger and protein kinetics were generated.

The data was analyzed based on the median fluorescence of both GFP and an anti-CD3 antibody-conjugated fluorochrome at different time points.

With respect to B2M-derived promoters, at the protein level, it can be observed that in B2M Enh5', the expression of GFP duly replicates the physiological expression of CD3. In the case of B2M, the expression of GFP increases in the interval of 0 to 8 hours, unlike in the case of CD3. Interestingly, B2M TetO vectors, in which the only difference with B2M is the insertion of the TetO operon 10 bp from the transcription start site, the expression pattern of GFP is more similar to that of CD3, as said increased expression is observed at 8 hours.

At the messenger RNA level, a pattern very similar to that of protein is observed, with the B2M Enh5' vector being the one that best mimics the CD3 pattern, followed by the B2M TetO promoter. However, in both cases, the decreased expression of eGFP at 8 hours is more pronounced that that observed in CD3. After 8 hours, the pattern between eGFP and CD3 is practically identical.

The Phenotype of the GFP+ T-Cells Changes Over Time to a State of High Differentiation.

Parallel to the study of the expression kinetics of GFP under the control of chimeric promoters in T-cells, a study of the time evolution of cellular phenotype was performed using, to that end, two antibodies, i.e., an anti-CD62L antibody and another anti-CD45RA antibody, a CD45 isoform which preserves all 3 exons, so it has the highest molecular weight of all the isoforms. The selective expression of these markers in the membrane allows distinguishing 4 phenotypes typical of T-cells: main memory T-cells, central memory T-cells, effector T-cells, and effector memory T-cells.

In the case of the B2M promoter, the 7-day cell population is still mostly the main memory cell population.

Generation of CAR+ T-Cells with Chimeric B2M Promoter.

Once the results were obtained using GFP as the transgene, the BM2 promoter was cloned into the CAR vector.

Once the promoter was cloned into the lentiviral backbone of third-generation CAR and the lentiviral vectors as described in detail in the materials and methods section were generated, T-cells were transduced with CAR vectors.

Figure 1A:
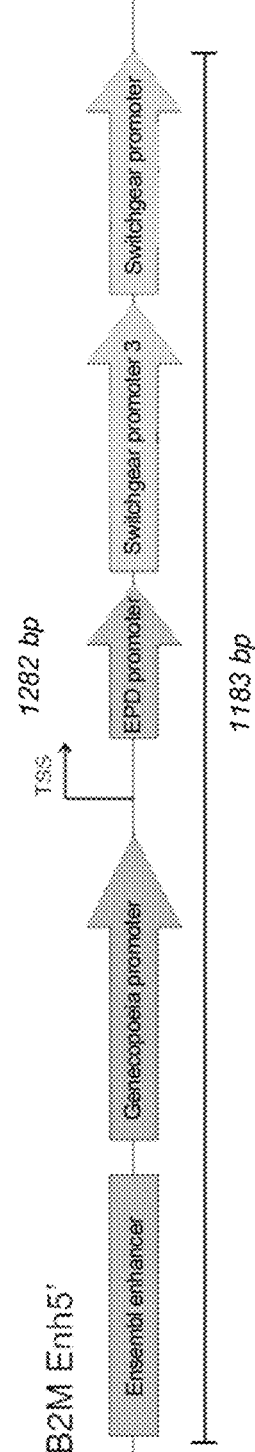
Figure 2:
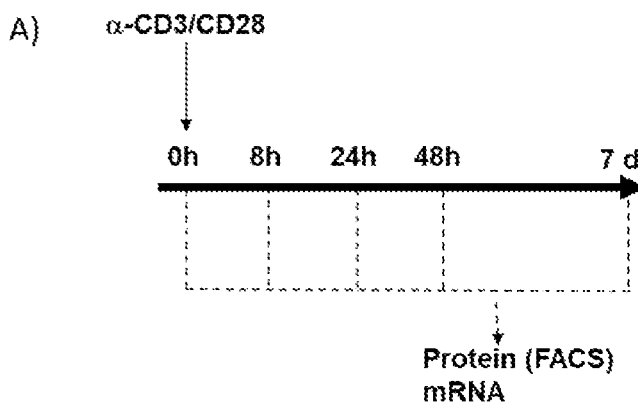
FIG. 2. Expression of the CD3/TCR protein decreases in response to anti-CD3/CD28 stimuli in primary T-cells. A) A pure population of human primary T-cells was isolated and stimulated with anti-CD3/CD28 (TransAct, Miltenyi) at 0 h and the expression of CD3 (an essential component of the T-cell receptor, TCR) was determined by means of FACS and mRNA analysis at the indicated times. B) Fold expression indicated the relative ratio between CD3 median fluorescence intensity in the CD3+ population in comparison with CD3 MeFI in the CD3 population divided by said expression at 0 h. Relative ratio=[CD3 MeFI of CD3+ gate/CD3 MeFI of CD3− gate at TIME]/CD3 MeFI of CD3+ gate/CD3 MeFI of CD3− gate at 0 h]. C) Fold expression refers to the relative ratio between CD3 mRNA in comparison with GAPDH mRNA (used as an internal control) divided by said expression at 0 h. Relative ratio=[expression of CD3/expression of GAPDH at TIME]/[expression of CD3/expression of GAPDH at 0 h].
Figure 2:
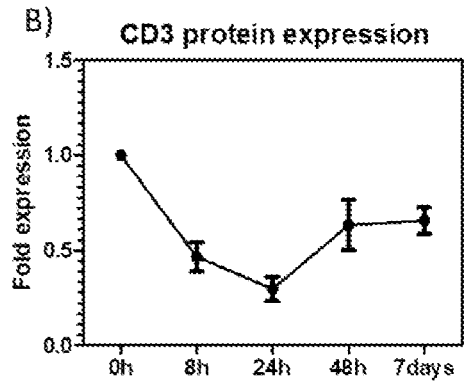
Figure 2:
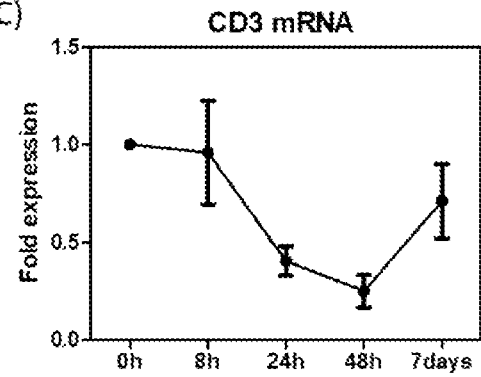
Figure 3:
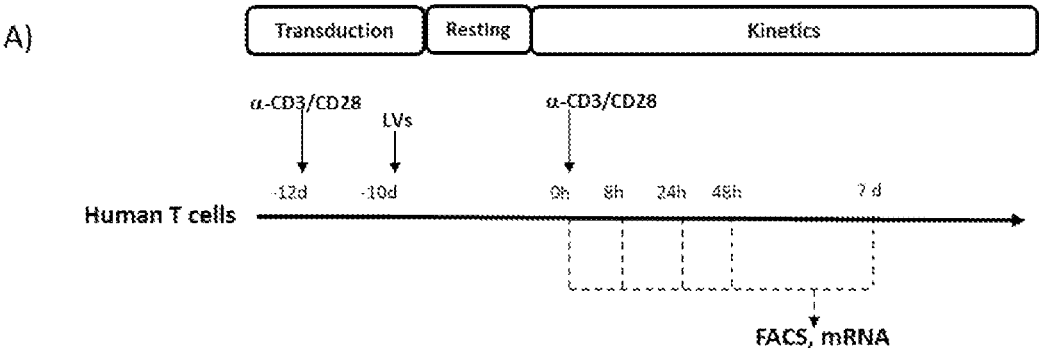
FIG. 3. GFP-directed expression by the chimeric B2M promoter imitated the CD3/TCR physiological pattern following activation in contrast to EF1-alpha promoter. A)
Figure 3:
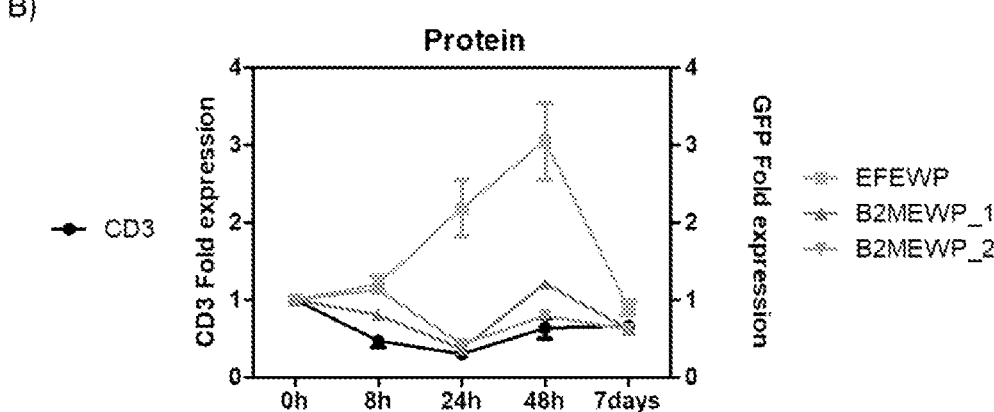
Figure 3:
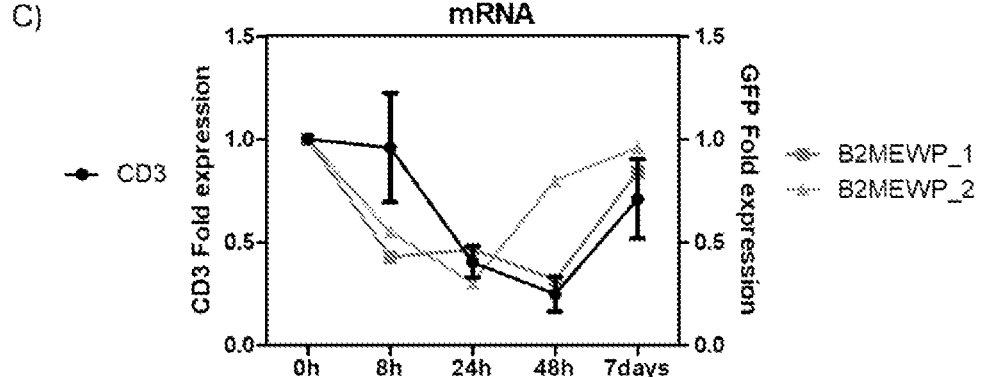

In this construct (FIG. 1 and FIG. 2), the LTRs allow integration. EGFRt encodes the receptor of truncated epidermal growth factor which allows depleting CAR+ cells, if necessary, (using a monoclonal antibody, cetuximab) and allows indirectly detecting the CAR using a fluorochrome-conjugated anti-EGFRt antibody. T2A is a self-cleaving peptide which allows cutting a long peptide into two short peptides (since CAR and EGFRt are encoded together as a recombinant protein and separated as a result of this mechanism). WPRE is a post-transcriptional regulatory element which enhances both the viral vector titer and the transgene expression.

Fresh T-cells processed by negative magnetic immunoselection from the mobilized peripheral blood of a healthy donor were used. Transduction was carried out by means of spinoculation using 50 µL of vector in 100,000 T-cells. The expression of CAR was determined 72 hours post-transduction. An expression of CAR of 18% was observed with the B2M promoter. CAR3G (the original lentiviral vector in which CAR is expressed under the control of the EF1-α promoter) was used as a positive staining and transduction control. NTD cells were used as a negative control.

The invention claimed is:

1. A polynucleotide consisting of SEQ ID NO: 1 or 2.

2. The polynucleotide of claim 1, consisting of SEQ ID NO: 1.

3. The polynucleotide of claim 1, consisting of SEQ ID NO: 2.

4. A gene construct comprising the polynucleotide according to claim 1.

5. The gene construct according to claim 4, wherein said gene construct is a viral vector.

6. The gene construct according to claim 5, wherein the viral vector is a lentiviral vector.

7. The gene construct according to claim 4, comprising a promoter operatively attached to a chimeric antigen receptor (CAR) comprising an extracellular ligand-binding domain, a transmembrane domain, and at least one intracellular signaling domain.

8. A cell transformed or transduced with a polynucleotide according to claim 1.

9. The cell according to claim 8, wherein said cell is an immune cell.

10. The cell according to claim 9, wherein said cell is selected from the group consisting of inflammatory lymphocytes, cytotoxic T lymphocytes, regulatory T lymphocytes, and helper lymphocytes.

\* \* \* \* \*

SEQUENCE LISTING

```
<160> NUMBER OF SEQ ID NOS: 14

<210> SEQ ID NO 1
<211> LENGTH: 1161
<212> TYPE: DNA
<213> ORGANISM: Artificial Sequence
<220> FEATURE:
<223> OTHER INFORMATION: synthetic sequence

<400> SEQUENCE: 1
aattcggcat gcttatcgat ttggtccttc cttacttgcc cctttcggcg gggagcaggg      60
gaggggtctg ggggaggcgt cgcccgggaa agcctgtctg ctgcagccta accagggctt     120
ttgcgggagc gcatggcttt tggctgtaat tcgtgcattt ttaacaaaaa cgcctgcctt     180
ctgcgtgaga ttctccagag caaactgggc ggcatgggcc ctgtggtctt ttcgtacaca     240
cggcttcctc tttggctctt tgcctggttg tttccaacat gtactgtgcc tcttactttc     300
ggttttgaaa acatgagggg gttgggcgtg gtagcttacg cctgtaatcc cagcacttag     360
ggaggccgag gcgggaggat ggcttgaggt ccgtagttga gaccagcctg ggctgctccg     420
gtggctgagg cgggaggatc tcttgagctt aggcttttga gcagaaagag aaaagaaaag     480
aaagaaagaa gtgtgaatac aatctcacaa aatcttgccg ccttccctca atcattttca     540
ataatcccaa cactttggga ggccaaggca ggctgatcac tctcaggaac tccaaagatt     600
caggtttact cacgtcatcc agcagagaat ggaaagtcaa atttcctgaa ttgctatgtg     660
tcctcactgt tcctcttaca aaagatctgt ggactccacc accacgaaat ggcggcacct     720
tatttatggt cacagaatga tgtacctaga gggcgctgga agctctaaag ccctagcagt     780
tactgctttt actattagtg gtcgtttttt tctccccccc gcccccgac aaatcaacag     840 aacaaagaaa attacctaaa cacttcttaa acatcacgag actctaagaa aaggaaactg     900
aaaacgggaa agtccctctc tctaacctgg cactgcgtcg ctggcttgga gacaggagac     960
ggtccctgcg ggccttgtcc tgattggctg ggccgcgttt aatataagtg gaggcgtcgc    1020
gctggcgggc attcctgaag ctgacagcat tcgggccgag tgtctcgctc cgtggcctta    1080
gctgtgctcg cgctactctc tctttctggc ctggaggcta tccagcgaga gactctccta    1140
ccctcccgct ggcgcgcccg g                                             1161

<210> SEQ ID NO 2
<211> LENGTH: 1264
<212> TYPE: DNA
<213> ORGANISM: Artificial Sequence
<220> FEATURE:
<223> OTHER INFORMATION: B2M_EWP2
```

-continued

<400> SEQUENCE: 2

```
gaattcggca tgcttatcga ttctcactgt tcctcttaga aaagatctgt ggactccacc      60
accacgaaat ggcggcacct tatttatggt cacacaatga tgtacctaga gggcgctgga     120
agctctaaag ccctagcagt tactgctttt actattagtg gtcgtttttt tctccccccc     180 gcccccgac aaatcaacag aacaaagaaa attacctaaa cacttcttaa acatcacgag     240
actctaagaa aaggaaactg aaaacgggaa agtccctctc tctaacctgg cactgcgtcg     300
ctggcttgga gacaggagac ggtccctgcg ggccttgtcc tgattggctg ggctcgcgtt     360
taatataagt ggaggcgtcg cgctggcggg cattcctgaa gcttccctat cagtgataga     420
gatctcccta tcagtgatag agagacagca ttcgggccga gtgtctcgct ccgtggcctt     480
agctgtgctc gcgctactct ctctttctgg cctggaggct atccagcgtg agtctctcct     540
accctcccgc tctggtcctt ccttacttgc ccctttcggc ggggagcagg ggaggggtct     600
gggggaggcg tcgcccggga aagcctgtct gctgcagcct aaccaggggct tttgcgggag     660 cgcatggctt ttggctgtaa ttcgtgcatt tttttttaag aaaaacgcct gccttctgcg     720
tgagattctc cagagcaaac tgggcggcat gggccctgtg gtcttttcgt acacacggct     780
tcctctttgg ctctttgcct ggttgtttcc aagatgtact gtgcctctta ctttcggttt     840
tgaaaacatg aggggggttgg gcgtggtagc ttacgcctgt aatcccagca cttagggagg     900
ccgaggcggg aggatggctt gaggtccgta gttgagacca gcctgggctg ctccggtggc     960
tgaggcggga ggatctcttg agcttaggct tttgagcaga aagagaaaag aaaagaaaga    1020
aagaagtgtg aatacaatct cacaaaatct tgccgccttc cctcaatcat tttcaataat    1080
cccaacactt tgggaggcca aggcaggctg atcactctca ggaactccaa agattcaggt    1140
ttactcacgt catccagcag agaatggaaa gtcaaatttc ctgtggtctt ttcgtacaga    1200
gggcttcgaa ttgctatgtg tctgtggtct tttcgtacac agggcttcgg cgcgcccggg    1260
atcc                                                                 1264
```

<210> SEQ ID NO 3
<211> LENGTH: 20
<212> TYPE: DNA
<213> ORGANISM: Artificial Sequence
<220> FEATURE:
<223> OTHER INFORMATION: primer Fw-cPPT

<400> SEQUENCE: 3

```
acagcagaga tccagtttgg                                                   20
```

<210> SEQ ID NO 4
<211> LENGTH: 18
<212> TYPE: DNA
<213> ORGANISM: Artificial Sequence
<220> FEATURE:
<223> OTHER INFORMATION: Primer Rv-eGFP

<400> SEQUENCE: 4

```
tcactctcgg catggacg                                                     18
```

<210> SEQ ID NO 5
<211> LENGTH: 21
<212> TYPE: DNA
<213> ORGANISM: Artificial Sequence
<220> FEATURE:
<223> OTHER INFORMATION: primer Fw cPPT-clinico

```
<400> SEQUENCE: 5
gtgcagggga aagaatagta g                                          21

<210> SEQ ID NO 6
<211> LENGTH: 20
<212> TYPE: DNA
<213> ORGANISM: Artificial Sequence
<220> FEATURE:
<223> OTHER INFORMATION: primer Rv CD19

<400> SEQUENCE: 6
tacaggactt tctttctgcc                                            20

<210> SEQ ID NO 7
<211> LENGTH: 20
<212> TYPE: DNA
<213> ORGANISM: Artificial Sequence
<220> FEATURE:
<223> OTHER INFORMATION: Fw GFP

<400> SEQUENCE: 7
aagctgaccc tgaagttcat                                            20

<210> SEQ ID NO 8
<211> LENGTH: 19
<212> TYPE: DNA
<213> ORGANISM: Artificial Sequence
<220> FEATURE:
<223> OTHER INFORMATION: Rev GFP

<400> SEQUENCE: 8
cgtcgtcctt gaagaagat                                             19

<210> SEQ ID NO 9
<211> LENGTH: 18
<212> TYPE: DNA
<213> ORGANISM: Artificial Sequence
<220> FEATURE:
<223> OTHER INFORMATION: Fw CD3

<400> SEQUENCE: 9
aagatgaagt ggaaggcg                                              18

<210> SEQ ID NO 10
<211> LENGTH: 18
<212> TYPE: DNA
<213> ORGANISM: Artificial Sequence
<220> FEATURE:
<223> OTHER INFORMATION: Rev CD3

<400> SEQUENCE: 10
ctcaggaaca aggcagtg                                              18

<210> SEQ ID NO 11
<211> LENGTH: 18
<212> TYPE: DNA
<213> ORGANISM: Artificial Sequence
<220> FEATURE:
<223> OTHER INFORMATION: Fw CD4

<400> SEQUENCE: 11
agaaagacgc aagcccag                                              18

<210> SEQ ID NO 12
<211> LENGTH: 18
```

-continued

```
<212> TYPE: DNA
<213> ORGANISM: Artificial Sequence
<220> FEATURE:
<223> OTHER INFORMATION: Rev CD4

<400> SEQUENCE: 12
gcagcaccag aagcaagt                                                      18

<210> SEQ ID NO 13
<211> LENGTH: 19
<212> TYPE: DNA
<213> ORGANISM: Artificial Sequence
<220> FEATURE:
<223> OTHER INFORMATION: Fw GAPDH

<400> SEQUENCE: 13
atggggaagg tgaaggtcg                                                     19

<210> SEQ ID NO 14
<211> LENGTH: 22
<212> TYPE: DNA
<213> ORGANISM: Artificial Sequence
<220> FEATURE:
<223> OTHER INFORMATION: Rev GAPDH

<400> SEQUENCE: 14
ggggtcattg atggcaacaa ta                                                 22
```